United States Patent
Tovey

(10) Patent No.: US 6,207,145 B1
(45) Date of Patent: *Mar. 27, 2001

(54) THERAPEUTIC APPLICATIONS OF HIGH DOSE INTERFERON

(75) Inventor: Michael Gerard Tovey, Paris (FR)

(73) Assignee: Pharma Pacific Pty Ltd., New South Wales (AU)

( * ) Notice: Subject to any disclaimer, the term of this patent is extended or adjusted under 35 U.S.C. 154(b) by 0 days.

This patent is subject to a terminal disclaimer.

(21) Appl. No.: 08/853,870

(22) Filed: May 9, 1997

(51) Int. Cl.$^7$ .................................................. A61K 38/21
(52) U.S. Cl. ...................... 424/85.4; 424/85.5; 424/85.6; 424/85.7
(58) Field of Search .................................... 424/85.4, 85.5, 424/85.6, 85.7

(56) References Cited

U.S. PATENT DOCUMENTS

| | | | |
|---|---|---|---|
| 4,605,555 | 8/1986 | Sato et al. | 424/85 |
| 5,019,382 | 5/1991 | Cummins, Jr. | 424/85.4 |
| 5,215,741 | 6/1993 | Young et al. | 424/85.7 |
| 5,286,748 | 2/1994 | Eby, III | 514/494 |

FOREIGN PATENT DOCUMENTS

| | | |
|---|---|---|
| 0 396 903 | 3/1990 | (EP) . |
| WO 82/00588 | 4/1982 | (WO) . |
| WO 92/10207 | 6/1992 | (WO) . |

OTHER PUBLICATIONS

Kaido, T.J., "Interanasal administration of IFN–α/β inhibits the development of visceral tumor metastases," *Journal of Interferon and Cytokine Research*, 17:31–36 (1997).

Yoshino, S., "The preventive effect of oral administration of Type 1 interferon on collagen–induced arthritis in rats," *Experimental and Molecular pathology*, 62:123–130 (1995).

Boguniewicz et al., "The Effect of Nebulized Recombinant Interferon–γ in Asthmatic Airways", *J. Allergy Clin. Immunol.* 95:133–135 (1995).

Brod et al., "Oral Administration of IFN–α is Superior to Subcutaneous Administration of IFN–α in the Suppression of Chronic . . . ", *Journal of Autoimmunity* 9:11–20 (1996).

Douglas et al., "Prophylactic Efficacy of Intranasal Alpha$_2$–Interferon Against Rhinovirus Infections in the Family Setting" 314: 65–70 (1986).

Hayden et al., "Intranasal Interferon α2 for Prevention of Rhinovirus Infection and Ilness", *Journal of Infectious Diseases* 148:543–550 (1983).

Hayden et al., "Human Tolerance and Histopathologic Effects of Long Term Administration of Intranasal Interferon–α2", *Journal of Infectious Diseases* 148:914–921 (1983).

Hayden et al., "Prevention of Natural colds by Contact Prophylaxis with Intranasal Alpha$_2$–Interferon", *New England Journal Of Medicine* 314:71–75 (1986).

Hayden et al., "Human Nasal Mucosal Responses to Topically Applied Recombinant Leukocyte A Interferon", *Journal of Infectious Diseases* 156:64–72 (1987).

Iida et al., "Protective Activity of Recombinant Cytokines Against Sendai Virus and Herpes Simplex Virus (HSV) infections in mice", *Vaccine* 7:229–233 (1989).

Machida et al., "Absorption of Recombinant Human Granulocyte Colony–Stimulating Factor (rhG–CSF) from Rat Nasal Mucosa", *Pharmaceutical Research* 10:1372–1377 (1993).

Matsuzawa et al., "Protective Effect of Mucosal Administration of Recombinant Human Macrophage Colony–Stimulating Factor . . . ", *Vaccine* 15:85–89 (1997).

Oehling et al., "Suppresion of the Immune System by Oral Glucocorticoid Therapy in Bronchial Asthma", *Allergy* 52:144–154.

Samo et al., "Efficacy and Tolerance of Intranasally Applied Recombinant Leukocyte A Interferon in Normal Volunteers", *Journal of Infectious Diseases* 148:535–542 (1983).

Samo et al., "Intranasally Applied Recombinant Leukocyte A Interferon in Normal Volunteers. II.", *Journal of Infectious Diseases* 150:181–188 (1984).

Soos et al., Oral Feeding of Interferon τ Can Prevent the Acute and Chronic Relapsing Forms of Experimental Allergic Encephalomyelitis, *Journal of Neuroimmunology* 75:43–50 (1997).

Takada et al., "Pharmacological Activity of Tablets Containing Recombinant Human Granulocyte . . . ", *International Journal of Pharmaceutics* 101:89–96 (1994).

Vriesendorp et al., "Oral Administration of Type I Interferon Modulates the Course of Experimental Allergic Neuritis", *Autoimmunity* 24:157–165 (1996).

Watanabe et al., "Absorption and Blood Leukocyte Dynamics of Recombinant Human Granulocyte Colony–Stimulating Factor . . . ", *International Journal of Pharmaceutics* 110:93–97 (1994).

Zielinska et al., "Comparison of the Long–Term Effects of Treatment with Oral and Parenteral . . . ", *Archivum Immunologiae et Therapiae Experimentalis* 44:359–366 (1996).

Hayden, Frederick G., "Intranasal Interferon α2 for Prevention of Rhinovirus Infection and Illness", The Journal of Infectious Diseases, vol. 148, No. 3 Sep. 1983. pp. 543–550.

Primary Examiner—Jerome D. Goldberg
(74) Attorney, Agent, or Firm—Browdy And Neimark

(57) ABSTRACT

Interferon composition for oromucosal contact to stimulate host defense mechanisms or an immune response in a mammal with a stimulating amount of the interferon which exceeds parenterally administered amounts of interferon, methods of treatment with such compositions and uses of interferon in the preparation of such oromucosal compositions.

15 Claims, No Drawings

THERAPEUTIC APPLICATIONS OF HIGH DOSE INTERFERON

This invention relates to methods of stimulation of host defense mechanisms against pathological conditions in a mammal by administration of high doses of interferon via the oromucosa. In particular, the invention is applicable to methods of treatment of autoimmune, neoplastic, neurodegenerative, parasitic, and viral diseases.

BACKGROUND OF THE INVENTION

Alpha interferons are used widely for the treatment of a variety of haematological malignancies including hairy cell leukaemia, chronic myelogenous leukaemia, low grade lymphomas, cutaneous T-cell lymphomas, and solid tumours such as renal cell carcinoma, melanoma, carcinoid tumours and AIDS-related Kaposi's sarcoma (Gutterman, J. U., *Proc. Natl. Acad. Sci. USA*, 1994 91: 1198–1205). Antitumour effects are usually seen at high dosage levels, often of the order of tens of millions of units of interferon-α (IFN-α), administered by parenteral injection. Interferon-β (IFN-β) is licensed for clinical use in treatment of relapsing-remitting multiple sclerosis and chronic viral hepatitis B and C.

Interferon-α and Interferon-β are both Type I interferons. Type I interferons are a large class of naturally-occurring cytokines which includes over 16 subclasses of IFN-α, plus IFN-β and IFN-ω. The Type I interferons bind to a single cell surface receptor, and stimulate a complex sequence of signal transduction events leading ultimately to anti-viral, anti-proliferative and other immunomodulatory effects, cytokine induction, and HLA class I and class II regulation (Pestka et al., *Annu. Rev. Biochem.*, 1987 56: 727). Individual subtypes of Type I IFN vary in activity. The most frequently observed amino acid at each position has been identified by scanning of a large number of allelic subtypes of IFN-α, and a synthetic Type I interferon having the consensus sequence has been synthesized (Alton et al in "The Biology of the Interferon System", E. de Maeyer and H. Schellekens eds. Elsevier (1983) 1991-128). This consensus interferon is commercially available (Infergen; Amgen, Inc.), and has recently been shown to have higher activity (w/w) than IFN-α2a or IFN-α2b; it has been suggested that consensus IFN would be clinically superior to IFN of an individual natural subtype (Blatt et al, *J. Interferon and Cytokine Research*, 1996 16: 489–499).

Although a number of routes of administration, including intravenous, subcutaneous, intramuscular, topical, and intralesional injection, are commonly employed for the administration of type I interferons, the oral route has not been generally used, because interferons are proteins which are considered to be inactivated by proteolytic enzymes and which are not absorbed appreciably in their native form in the gastrointestinal tract. Indeed a number of studies have failed to detect interferons in the blood following oral administration (Cantell and Pyhäla, *J. Gen. Virol.*, 1973 20: 97–104; Wills et al, *J. IFN Res.*, 1984 4: 399–409; Gilson et at, *J. IFN Res.*, 1985 5: 403–408).

It is widely considered that in order to obtain the maximum therapeutic effect, the highest possible dose of interferon should be used. Although the availability of recombinant material has meant that very high dose levels are feasible, in practice it has been found that the side-effects of interferon administration have severely limited the dose of interferon which can be used and the duration of treatment. These side-effects include severe malaise and depression, leading in some cases even to suicide. A recent editorial by Hoofnagle in the New England Journal of Medicine has summarized these problems (Hoofnagle, J. H., and Lau, D., *New Eng. J. Medicine* 1996, 334:, 1470–1471). Meta-analysis of the effect of interferon-α treatment in patients with hepatitis B e antigen-positive chronic hepatitis B has shown a rate of remission of 25 to 40%, in patients with typical chronic hepatitis B, treated with 5 million IU daily or 10 million IU three times per week for 3 to 6 months. These results fall short of a cure, however, as most patients remain positive for hepatitis surface antigen and harbour viral DNA when tested by the polymerase chain reaction. Furthermore, these doses of interferon are poorly tolerated, and 10% to 40% of patients require dose reduction due to intolerable side effects. At a well-tolerated dose of 1 million IU daily, the remission rate is, however, only 17% (Perrillo et al. *New Eng. J. Medicine*, 1990, 323:, 295–301). In patients with chronic hepatitis C, sustained long-term improvement is associated with the loss of HCV RNA, which occurs in only 10 to 20% of patients treated with a dose of 3 million IU three times per week for 6 months (Hoofnagle and Lau, op. cit.). In patients with cancer, significant response rates are usually seen only at the highest tolerated doses of interferon-α. Thus in patients with multiple myeloma, for example, the response rate is 50% in patients treated with 20 to 30 million IU daily, and only 15 to 20% in patients treated with 3 million IU. Very few patients are able, however, to tolerate the high-dose regimen for more than a short period of time (Ahre et al. *Eur. J. Hematol.*, 1988, 41:, 123–130). Thus clearly there is a need in the art for means which would enable the administration of high dose interferon without the induction of severe side-effects.

There have been a number of anecdotal reports of efficacy of low doses of interferon administered as a nasal spray or as an oral liquid formulation in the treatment of a variety of viral conditions, particularly influenza. However, in most of these reports the interferon preparations used were relatively crude. Placebo-controlled trials of relatively high dose intra-nasal interferon for treatment of rhinovirus infection showed that the treatment was effective, but that there was a significant incidence of side-effects (Hayden et al, *J: Infect. Dis.*, 1983 148: 914–921; Douglas et al, *New Engl. J. Med.*, 1986 314: 65–80; Hayden et al, *New Engl. J. Med.*, 1986 314: 71–75).

More recently a series of patent specifications has described the use of low doses of orally administered interferon of heterologous species origin for the treatment of infectious rhinotracheitis ("shipping fever") in cattle, and of feline leukaemia, and also treatment of other conditions, for enhancement of efficiency of vaccines; for improving the efficiency of food utilisation; and for prevention of bovine theileriosis. See U.S. Pat. No. 4,462,985, Australian Patent No. 608519, Australian Patent No. 583332 and U.S. Pat. No. 5,215,741 respectively. In addition U.S. Pat. No. 5,017,371 discloses the use of interferon in this way for treatment of side-effects of cancer chemotherapy or radiotherapy. In these specifications, the interferon used was human interferon-α prepared by the method of Cantell, administered in phosphate buffered saline, at a dose of 0.01 to 5 IU per pound body weight. While these specifications suggest that such low doses of interferon administered to the oropharyngeal mucosa, preferably in a form adapted for prolonged contact with the oral mucosa, may be efficacious for treatment of a wide variety of conditions including cancer, the experimental evidence for conditions other than shipping fever, feline leukaemia, canine parvovirus and theileriosis is largely anecdotal. In particular, no properly controlled trials of this treatment in any animal model for human cancers are presented.

More recent studies on the effects of very low doses of interferon administered by the oral or oropharyngeal mucosa have been reviewed (Bocci, *Clin. Pharmacokinet.*, 1991 21: 411–417; *Critic. Rev. Therap. Drug Carrier Systems*, 1992 9: 91–133; Cummins and Georgiades, *Archivum Immun. Therap. Exp.*, 1993 41: 169–172). It has been proposed that this type of treatment is particularly useful for treatment of HIV infection, and can at least improve quality of life in AIDS patients (Kaiser et al, AIDS, 1992 6: 563–569; Koech et al, *Mol. Biol. Ther.*, 1990 2: 91–95). However, other reports indicate that such treatments provide no clinical benefit. A Phase I study of use of oral lozenges containing low doses of interferon for treatment of hepatitis B has also been reported (Zielinska et al, *Archiv. Immunol. Therap. Exp.*, 1993 41: 241–252).

In Australian Provisional Patent Application No. PN 9765, low doses of interferon administered to the oropharyngeal cavity by the oromucosal route were shown to be effective in protecting mice against challenge with highly metastatic tumour cells (Friend Erythroleukemia). The quite exceptional nature of these results, together with the fact that very few substances exhibit activity against these very aggressive tumours, indicates that administration of interferon to the oropharyngeal cavity may be useful in the treatment of cancer. Low oromucosal doses of interferon were also effective in treating mice injected intraperitoneally with encephalomyocarditis virus (EMCV), which normally gives rise to a rapidly progressing fatal disease characterized by central nervous system involvement and encephalitis. Although this system is a very severe test of antiviral activity, the oromucosal route for administration of interferon was comparably effective to intraperitoneal administration.

The disclosure of all patents and publications referred to in this specification are incorporated by reference herein.

SUMMARY OF THE INVENTION

This invention provides a method for stimulating host defense mechanisms in a mammal via the oromucosal administration of an interferon at doses higher than those which induce a pathological response when administered parenterally, generally greater than about $20 \times 10^6$ IU of homologous interferon-$\alpha$ in man.

In one aspect, the invention may be considered as a method of stimulating the immune response in a mammal by administering to the mammal an immunostimulating amount of an interferon via oromucosal contact, said amount being in excess of a dose of the same interferon as that which induces a pathological response when administered parenterally, generally greater than about $20 \times 10^6$ IU of homologous interferon-$\alpha$ in man.

Alternatively, the invention provides a method for increasing the therapeutic index of interferon by administering interferon oromucosally.

The oromucosal administration may involve administering an effective dose of interferon in a single dose or the effective dose may be administered in a plurality of smaller doses over a period of time sufficient to elicit immunostimulation equivalent to that of a single dose. Likewise, the dose of interferon may be administered continuously over a period of time sufficient to induce an effect equivalent to that of a single dose.

In its applied aspects, the invention provides a method for treating autoimmune, mycobacterial, and neurodegenerative diseases, neoplastic conditions and viral infections, via administering to the mammal an effective amount of an interferon via oromucosal contact, said amount being in excess of the dose of the same interferon which induces a pathological response when parenterally administered. In particular, the invention provides a method for treating autoimmune diseases such as arthritis, diabetes mellitus, lupus SLE, and multiple sclerosis, mycobacterial diseases such as leprosy and tuberculosis, neurodegenerative disorders such as spongiform encephalitis and Creutzfeldt-Jakob disease, parasitic diseases such as malaria, and viral diseases such as genital herpes, hepatitis B and C, HIV, HPV, and HSV-1 and 2.

The invention also provides a method for treating multiple myeloma, hairy cell leukemia, chronic myelogenous leukemia, low grade lymphoma, cutaneous T-cell lymphoma, carcinoid tumors, cervical cancer, sarcomas including Kaposi's sarcoma, kidney tumors, carcinomas including renal cell carcinoma, hepatic cellular carcinoma, nasopharyngeal carcinoma, hematologic malignancies, colorectal cancer, glioblastoma, laryngeal papillomas, lung cancer, colon cancer, malignant melanoma, and brain tumors including malignant brain tumors. In one embodiment, the method is generally applicable in the treatment of tumors of non-viral etiology.

In another embodiment, the invention provides a pharmaceutical composition for oromucosal administration comprising a therapeutically effective amount of at least one interferon, said amount exceeding that amount which induces a pathological response when administered parenterally, and a pharmaceutically acceptable carrier. The composition may be provided as a solution, tablet, lozenge, gel, syrup, paste, or controlled release oromucosal delivery system. Optionally, the composition may contain buffers, stabilizers, thickening agents, absorption and viscosity enhancers, and the like.

In one embodiment, the pharmaceutical composition is provided in unit dosage form having from about $20 \times 10^6$ IU to about $1000 \times 10^6$ IU of interferon, preferably from about $20 \times 10^6$ IU to about $500 \times 10^6$ IU, preferably from about $50 \times 10^6$ IU to about $500 \times 10^6$ IU.

The method may be practiced either as the sole therapeutic approach, or as an adjunct to radiation therapy, chemotherapy, or with other cytokines, such as interleukin-2, 12, or 15, or with IFN-inducers.

The method is preferably conducted using a Type I or Type II IFN, selected from $\alpha$, $\beta$, $\gamma$, $\omega$, and consensus interferons, most preferably with a recombinant IFN-$\alpha$.

DETAILED DESCRIPTION OF THE INVENTION

The invention will now be described in detail by way of reference only using the following definitions and examples. All patents and publications referred to herein are expressly incorporated by reference.

Definitions

As used herein, "interferon" refers to a Type I or Type II interferon, including those commonly designated as $\alpha$, $\beta$, $\gamma$, and $\omega$, and mixtures thereof, including the consensus sequence. Interferons are available from a wide variety of commercial sources and are approved for the treatment of numerous indications. The interferon may be from natural sources, but is preferably a recombinant product. For the purposes of the invention, the term "interferon" also includes polypeptides or their fragments which have interferon activity, and chimeric or mutant forms of interferon in which sequence modifications have been introduced, for example to enhance stability, without affecting the nature of their biological activity, such as disclosed in U.S. Pat. Nos. 5,582,824, 5,593,667, and 5,594,107 among others.

By the term "high dose" is meant a dose greater than the maximum dose usually tolerated of the same interferon when given by a parenteral route, such as intravenous or intraperitoneal administration. As currently envisioned, a high dose of interferon is greater than about $0.28 \times 10^6$ IU/KG body weight or about $20 \times 10^6$ IU of homologous interferon-α for a 70 kg human. Preferably the dose is greater than about $30 \times 10^6$ IU. In a particularly preferred form of the invention the total dose is from about $20 \times 10^6$ IU to about $1000 \times 10^6$ IU, more preferably from about $20 \times 10^6$ IU to $500 \times 10^6$ IU, most preferably from about $50 \times 10^6$ IU to about $500 \times 10^6$ IU. As used herein, "high dose" is generally considered to be a therapeutically effective dose when administered oromucosally, which if given parenterally would induce a pathological response, either manifested by the appearance of unacceptable side effects or surrogate markers of toxicity. The definition of high dose is of necessity flexible, since it may vary depending, inter alia, upon the individual sensitivity, size, weight, and age of the patient, the nature and severity of the condition being treated, the particular interferon used and the specific vehicle of administration. A physician treating a patient with a particular interferon will be able to readily identify the suitable high dose range for the patient to be treated. For other types of interferon the dose that will induce a pathological response may differ from that of homologous interferon-α in man.

Optionally the interferon may be administered concurrently with an inducer of interferon synthesis and release. The inducer may be administered together with the interferon, or may be administered separately. Inducers of interferon include, for example, polynucleotides such as poly I:C; preferably a low molecular weight, orally administrable interferon inducer is used. Suitable inducers are known in the art, for example, Tilorone (U.S. Pat. No. 3,592,819; Albrecht et al, *J. Med. Chem.* 1974 17: 1150–1156) and the quinolone derivative Imiquimod (Savage et al; *Brit. J. Cancer*, 1996 74: 1482–1486).

The methods and compositions of the invention may optionally be used in conjunction with one or more other treatments for the specific condition, and the attending physician or veterinarian will readily be able to select such other treatment as may be appropriate in the circumstances.

In one embodiment, the invention provides a method of treatment of a neoplastic condition in a mammal, comprising the step of administering interferon as described above. The neoplastic condition may be metastatic cancer.

While the method of the invention may be used without concurrent treatment with other agents, it is contemplated that this embodiment of the invention will be particularly useful in the following settings:

a) as adjuvant therapy, subsequent to surgery, chemotherapy, or radiotherapy given by standard protocols;

b) for treatment of interferon-sensitive neoplasias, the method of the invention is utilized either alone or in conjunction with conventional chemotherapy or radiotherapy; and c) for treatment of interferon-resistant neoplasias, the method of the invention is utilized either alone or most preferably in conjunction with conventional chemotherapy or radiotherapy.

The above methods are directed at inducing and/or maintaining remission of disease. By "in conjunction with other treatment" is meant that the interferon is administered before, during and/or after the radiotherapy or other chemotherapy. The most suitable protocol will depend on a variety of factors, as discussed below.

In particular, it is contemplated that the method of the invention will preferably be used in conjunction with at least one other treatment selected from the group consisting of chemotherapy using cytostatic drugs, one or more other cytokines which have anti-cancer activity but which have a different mechanism of action from that of interferon, anti-angiogenic agents, and agents which potentiate the activity of interferon. Preferably the second cytokine is interleukin-1 (IL-1), interleukin-2 (IL-2) interleukin-12 (IL-12), or interleukin-15 (IL-15); preferably the angiogenesis inhibitor is AGM-1470; preferably the interferon-potentiating treatment is hyperthermia or arginine butyrate.

Preferred cytostatic drugs to be administered in conjunction with interferon include but are not limited to cyclophosphamide, cisplatin, carboplatin, carmustine (BCNU; N,N-Bis(2-chloroethyl)-N-nitrosourea), methotrexate, adriamycin, α-difluoromethylornithine, and 5-fluorouracil.

The neoplastic conditions susceptible to this method include but are not limited to cancers which respond to parenteral administration of high doses of IFN-α, such as hematological malignancies, multiple myeloma, hairy cell leukemia, or chronic myelogenous leukemia, low grade lymphomas, cutaneous T cell lymphoma, solid tumors such as renal cell carcinoma and melanoma, carcinoid tumors, or AIDS-associated Kaposi's sarcoma, in particular malignant tumors of non-viral etiology. The viral condition may be an acute or fulminant infection, such as rhinovirus, influenza, herpes varicella, herpes zoster, dengue fever, or viral encephalitis including but not limited to measles virus encephalitis, Murray Valley encephalitis, Japanese B encephalitis, tick-borne encephalitis and Herpes encephalitis; haemorrhagic fevers such as Ebola virus, Marburg virus, Lassa fever; Hanta virus infections, and other viral infections thought to be transmitted from animals to humans, such as equine morbillivirus. In many of these conditions there is no treatment and/or vaccine presently available, and supportive treatments may be inadequate. Alternatively the viral condition may be the result of chronic infection, such as hepatitis B, hepatitis C, hepatitis D or other forms of viral hepatitis, and CMV, HIV, HPV, and HSV I & II infection. Hepatitis B and hepatitis C are both currently treated with parenteral interferon; long-term interferon treatment in HIV infection which has progressed to AIDS is under clinical trial.

In a second embodiment, the disease to be treated is malaria, and again a Type I or II interferon is administered as described above. The causative organism of the malaria may be *Plasmodium malariae, Plasmodium vivax, Plasmodium falciparum* or *Plasmodium ovale*. It is particularly contemplated that the method of the invention will protect against progression of malaria to the cerebral form.

In a third embodiment, the invention provides a method of treatment of autoimmune disorders such as HIV, rheumatoid arthritis, and multiple sclerosis, whether of the relapsing-remitting or the chronic progressive type or immunodeficiencies such as AIDS, comprising the step of administering an interferon as described above.

Again the method and dosage form of the invention may be used in conjunction with other treatments. For example, for herpes virus infection acyclovir or ganciclovir may be used. For HIV infection azidothymidine (zidovudine) or one or more other HIV reverse transcriptase inhibitors, and/or HIV protease inhibitors may be used.

In the preparation of the pharmaceutical compositions of this invention, a variety of vehicles and excipients for IFN may be used, as will be apparent to the skilled artisan. Representative formulation technology is taught in, inter alia, Remington: The Science and Practice of Pharmacy, 19th ed., Mack Publishing Co., Easton, Pa., 1995, and its predecessor editions. The IFN formulation may comprise stability enhancers, such as glycine or alanine, as described in U.S. Pat. No. 4,496,537, and/or one or more carriers, such as a carrier protein. For example, for treatment of humans pharmaceutical grade human serum albumin, optionally together with phosphate-buffered saline as diluent, is commonly used. Where the excipient for IFN is human serum albumin, the human serum albumin may be derived from human serum, or may be of recombinant origin. Normally when serum albumin is used it will be of homologous origin.

The IFN may be administered by any means which provides contact of the IFN with the oromucosal cavity of the recipient. Thus it will be clearly understood that the invention is not limited to any particular type of formulation. The present specification describes administration of IFN deep into the oromucosal cavity; this may be achieved with liquids, solids, or aerosols, as well as nasal drops or sprays. Thus the invention includes, but is not limited to, liquid, spray, syrup, lozenges, buccal tablets, and nebuliser formulations. A person skilled in the art will recognize that for aerosol or nebuliser formulations the particle size of the preparation may be important, and will be aware of suitable methods by which particle size may be modified.

In one aspect, the interferon is administered in a single dose. Alternatively, the interferon is administered in a plurality of lower doses, distributed over time, so that the net effect is equivalent to the administration of the single higher dose. One approach to this delivery mode is via the provision of a sustained or controlled release device adhered to or implanted in the oromucosal cavity and designed to release interferon over time in an amount equivalent to a single high dose.

Representative formulations of interferon for oromucosal use include the following (all % are w/w):

Tablet: Dextrose BP 45%; gelatin BP 30%; wheat starch BP 11%; carmellose sodium BP 5%; egg albumin BPC 4%; leucine USP 3%; propylene glycol BP 2%; and $50 \times 10^6$ IU IFN-α2. The tablet may be used as is and allowed to slowly dissolve in the mouth or may be dissolved in water and held in the mouth in contact with the oromucosa as needed.

An interferon paste may be prepared, as described in U.S. Pat. No. 4,675,184, from glycerin 45%, sodium CMC 2%, citrate buffer (pH 4.5) 25%, distilled water to 100%, and $50 \times 10^6$ IU IFN-α2 The interferon paste may be adhered to the buccal mucosa.

Likewise, a gargle or a syrup may be prepared by adding the desired amount of interferon to a commercially available mouthwash or cough syrup formulation.

Within the specific dose ranges referred to above, the optimal treatment in any individual case will depend on the nature of the condition concerned, the stage of disease, previous therapy, other, continuing therapy, the general state of health of the mammal, the sensitivity of the subject to interferon, etc., and therefore will be at the physician's or veterinarian's discretion, bearing in mind all these circumstances. The length of treatment will of course vary with the condition being treated, for example, treatment of a slow-growing cancer, such as prostate cancer, would be expected to involve a different course of treatment than treatment of a rapidly growing cancer, such as hepatic cellular carcinoma. Similarly, an acute infection such as caused by Ebola virus would be expected to involve a different course of treatment than a chronic condition, such as hepatitis.

The effective dose disclosed herein is one which may generate a pathological response in the mammal when administered parenterally, but is both effective and either non-toxic or less toxic when administered oromucosally. A pathological response may be acute, chronic, or cumulative, and may be manifested by changes in blood chemistry, such as leukopenia, bone marrow depression, or other histological parameters. As used herein, a pathological response includes adverse side effects, such as fever, malaise, or flu-like symptoms, vascular reactions, such as phlebitis, and local inflammatory reactions at the site of injection. Such responses will vary considerably among the patient population in view of individual variations in sensitivity to interferon.

For many patients, it is expected that oromucosal doses will exceed those known to be tolerated in existing approved parenteral protocols. In one embodiment, the total dose may be administered in multiple lower doses over time, or even may be delivered continuously or in a pulsatile manner from a controlled release device adhered to or implanted in the oromucosa.

INTERFERONS AND INTERFERON FORMULATIONS

Mouse IFN-α/β

Mouse IFN-α/β (Mu IFN-α/β) was prepared from cultures of C243-3 cells induced with Newcastle disease virus (NDV) and purified as described previously (Tovey et al, *Proc. Soc. Exp. Biol. and Med.*, 1974 146: 809–815). The preparation used in this study had a titer of $4 \times 10^6$ International Units (IU)/ml and a specific activity of $5 \times 10^7$ IU/mg protein as assayed on mouse 929 cells challenged with vesicular stomatitis virus (VSV) as described previously (Tovey et al, *Proc. Soc. Exp. Biol. and Med.*, 1974 146: 809–815). The preparation was standardized against the international reference preparation of murine IFN-α/β of the National Institutes of Health (NIH) (G-002-9004-5411).

Human IFN-α-1-8

Recombinant human IFN-α 1-8 (Hu IFN-α 1-8; BDBB lot no. CGP 35269-1, Ciba-Geigy, Basel, Switzerland) was prepared and purified as described previously (Meister et al, *J. Gen. Virol.*, 1986 67:1633–1643). The preparation used in this study had a titer of $70 \times 10^6$ IU/ml on homologous human WISH cells challenged with VSV as described previously (Tovey et al, *Nature*, 1977 267: 455–457), and a titer on heterologous mouse L929 cells of $1 \times 10^6$ IU/ml. The preparation was standardized against both the NIH human IFN-α international reference preparation (G-023-901-527) and the NIH murine IFN-α/β standard (G-002-9004-5411). The specific activity of the IFN preparation was $2 \times 10^8$ IU/mg protein.

RECOMBINANT MURINE INTERFERON-α

Recombinant murine interferon-a was purchased from Life Technologies Inc. The preparation used in this study (lot no. HKK404) had a titer of $6 \times 10^6$ IU/ml and a specific activity of $6 \times 10^8$ IU/mg protein as assayed on mouse L929 cells challenged with VSV (Tovey et al, Proc. Soc. Exp. Biol. Med., 1974, 146:406–415).

RECOMBINANT MURINE INTERFERON β

Recombinant murine interferon β was purchased from R & D Systems Inc. The preparation used in this study (lot no.

1976-01S) had a titer of $3.2 \times 10^4$ IU/ml and a specific activity of $8 \times 10^6$ IU/mg protein as assayed on mouse L929 cells challenged with VSV (Tovey et al, *Proc. Soc. Exp. Biol. Med.*, 1974, 146:406–415).

RECOMBINANT MURINE INTERFERON γ

Recombinant murine interferon γ was purchased from R & D Systems Inc. The preparation used in this study (2580-03SA) had a titer of $2 \times 10^5$ IV/ml and a specific activity of $1 \times 10^7$ IU/mg protein as assayed on mouse L929 cells challenged with VSV (Tovey et al, *Proc. Soc. Exp. Biol. Med.*, 1974, 146:406–415).

All the interferon preparations were titrated simultaneously in the same assay and standardized against the international reference preparation of murine interferon α/β of the US National Institutes of Health (G-002-9004-5411).

EXCIPIENT

Interferon preparations were diluted either in phosphate buffered saline (PBS) containing bovine serum albumin (BSA) or in the proprietary excipient described below. Bovine serum albumin fraction V (RIA grade; immunoglobulin free; Cat. no. A7888; Sigma; USA) was dissolved at a final concentration of 100 μg/ml in PBS (pH 7.4) and sterilized by filtration (0.2 μ, Millex-GV, Millipore, USA). The proprietary excipient used was as follows, supplied in the form of tablets (Ferimmune™, Pharma Pacific):

|  | % w/w | mg/tablet |
| --- | --- | --- |
| Dextrose (Glucose) BP** | 44.67*** | 55.84 |
| Gelatin BP** | 30.06 | 37.58 |
| Wheat Starch BP** | 11.31 | 14.14 |
| Carmellose Sodium BP** | 4.96 | 6.20 |
| Egg Albumen BPC** | 4.03 | 5.04 |
| Leucine USP | 3.00 | 3.75 |
| Propylene Glycol BP | 1.88 | 2.35 |
| Dextran 40** | 0.06 | 0.08 |
| (as Dextran 40 Injection BP) |  |  |
| Sodium Phosphate BP | 0.03 | 0.04 |
| Sodium Chloride BP | 0.01 | 0.01 |
| Sodium Acid Phosphate BP | 0.01 | 0.01 |
| Total | 100.02 | 125.04 |

**Calculated on an anhydrous basis
***Derived from:
Dextrose (Glucose) BP (anhydrous) 44.64%
Glucose BP (as Dextran 40 Injection BP) 0.03%

A single tablet was dissolved in 1.5 ml phosphate buffered saline, centrifuged at 16,000 g for 15 m, and then sterile filtered (0.2 μ, Millex-GV, Millipore, USA), and stored at 4° C. prior to use. Excipient was prepared daily prior to use.

INTERFERON DELIVERY SYSTEM

Preliminary experiments showed that the application of 5 μl of crystal violet to each nostril of a normal adult mouse using a P20 Eppendorf micropipette resulted in an almost immediate distribution of the dye over the whole surface of the oropharyngeal cavity. Staining of the oropharyngeal cavity was still apparent some 30 minutes after application of the dye. Essentially similar results were obtained using $^{125}$I-labeled recombinant human IFN-α 1–8 applied in the same manner. This method of administration was therefore used in all subsequent experiments.

For the purposes of the animal experiments described in this specification, it will be clearly understood that the expressions "oromucosal" or "oropharyngeal" or "intranasal/oral" or "intranasal plus oral" or "in/or" with reference to the route of administration of IFN is to be taken to mean administration of the IFN preparation deep into the nasal cavity so that it is rapidly distributed into the oromucosal cavity, i.e. the mouth and throat of the recipient mammal, so as to make contact with the mucosa lining this cavity.

EMCV (ENCEPHALOMYOCARDITIS VIRUS)

| | |
| --- | --- |
| Batch: | Lot no. 095001 |
| Expiration Date: | December 1997 |
| Preparation: | EMCV strain JH was propagated on mouse L929 cells using methods described previously (Gresser I. Bourali C, Thomas MT, Falcoff E. Effect of repeated inoculation of interferon preparations on infection of mice with encephalomyocarditis virus Proc Soc Exp Biol Med 1968 Feb; 127:491–6) |
| Characterization: | The virus stock used in this study had a titer of $5 \times 10^{8.62}$TCID$_{50}$ on mouse L929 cells. |
| Storage: | Stock EMCV was stored at −70° C. A power cut on day 1 of the Virus Titration necessitated transfer temporarily to back-up storage at approximately the same temperatures. The material remained frozen at all times. On day +8 of the Virus Titration the −70° C. freezer increased in temperature to −60° C. Diluted EMCV was prepared immediately before use and was kept on ice or in the animal room refrigerator until use. |

FRIEND ERYTHROLEUKAEMIA CELLS

The IFN-α/β-resistant clone, 3C18, of Friend erythroleukaemia cells (FLC) was obtained from Dr E. Affabris, Rome and is described in detail by Affabris et al, 1982 (*Virology*, 120: 441–452). These cells were subsequently maintained by in vivo passage. Briefly, DBA/2 mice were inoculated by intraperitoneal injection (ip) with approximately 100 LD$_{50}$ of 3C18 cells and one week later the tumor cells were harvested from the peritoneum of the mice, counted and other mice were again inoculated with 100 LD$_{50}$ of 3C18 cells. This procedure was repeated for 60 to 100 passages. It has been shown that the 3C18 cells used at the 60th to 100th in vivo passage are highly metastatic for the liver and spleen (Gresser et al, *Int. J. Cancer*, 1987 39: 789–792). The phenotype of IFN resistance was confirmed routinely by cultivating the in vivo passaged cells in vitro in the presence of IFN-α/β (Belardelli et al, *Int. J. Cancer*, 1982 30: 813–820).

L1210R6 CLONE & EL4 TRANSPLANTABLE TUMOR

The interferon-α/β-resistant clone, L1210R6, of L1210 lymphoma cells was isolated in our laboratory (Gresser et al., 1974, Interferon and cell division. IX. Interferon-Resistant L1210 Cells: Characteristics and Origin. *J. Nat. Cancer Inst.*, 52:553–559).

The EL4 transplantable tumor was originally derived from mice inoculated with the chemical carcinogen 1-2 dimethyl benzanthrein (Gorer, Pa., 1950, *Br. J. Cancer*, 4:372–381).

The L1210 lymphoma cells were maintained by serial in vivo passage in specific-pathogen free DBA/2 mice.

The EL4 tumor was maintained by serial in vivo passage in specific-pathogen free C57BL/6 mice.

B16 MELANOMA

The B16 melanoma is a transplantable tumor of spontaneous origin derived from a C57BL/6 mouse (Fidler I. J. and Kriple, M. L. 1977, Science 197, 893–897). The B16 melanoma is a rapidly growing, highly anaplastic, melanin producing tumor which metastasiz principally to the lung. The B16 melanoma is considered to be a good model for rapidly growing, highly aggressive human tumors.

B16 melanoma cells were maintained by serial in vivo passage in specific-pathogen free C57BL/6 mice.

ANIMALS

The mice used in this study were obtained from a specific pathogen-free colony (IFFA CREDO, France). They were housed in a specific pathogen-free animal facility at the Institut Federatif CNRS at Villejuif according to EEC standards.

INTERFERON BIOASSAY

Interferon was assayed according to a conventional method. Briefly, samples (20 µl) were diluted in 80 µl of Eagle's Minimal Essential Medium (MEM) (Gibco, France) containing 2% heat-inactivated Fetal Calf Serum (FCS) (Gibco, France) and added to each well of a microtitre plate (Falcon, cat. no. 3072) using a multichannel micro-pipette (Finnpipette, Labsystem, 50–300 µl). WISH or L929 cells ($2\times10^4$ cells/well) were added in 100 µl of MEM containing 2% FCS and incubated overnight at 37° C. in an atmosphere of 5% $CO_2$ in air (Forma 3029 $CO_2$ incubator). The cells were then examined for any signs of toxicity using an Olympus IM GLDW inverted microscope equipped with a 10× objective. Samples which did not exhibit detectable toxicity were then subjected to serial two-fold dilutions starting from an initial 1:10 dilution in a total volume of 200 µl of Eagle's MEM containing 2% FCS, by carrying forward 100 µl of diluted material with a multichannel micropipette, in a microplate containing 100 µl per well of fresh Eagle's MEM containing 2% FCS, Appropriate serial two-fold dilutions of the NIH human IFN-α reference standard (G-023-901-527) or the NIH Mu IFN-α/β reference standard (G-002-9004-5411) were also prepared. WISH or L929 cells ($2\times10^4$ cells/well) in 100 µl of Eagle's MEM containing 2% FCS were then added to each plate where appropriate and incubated overnight at 37° C. in an atmosphere of 5% $CO_2$ in air. The cell monolayers were then checked for any signs of toxicity and in the absence of any apparent toxicity, the culture was aspirated and replaced with 200 µl of Eagle's MEM containing 2% FCS containing 100 $TCID_{50}$ of VSV ($2\times10^{-4}$ $VSV_{23}$ for WISH cells, or $10^{-5}$ $VSV_{23}$ for L929 cells). The plates were then incubated overnight at 37° C. in an atmosphere of 5% $CO_2$ in air. The cell monolayers were then examined for specific viral cytopathic effect using an Olympus IM ULWD inverted microscope. Interferon titers were determined from the reciprocal of the dilution which gave 50% protection against specific viral cytopathic effect, and are expressed in international reference units/ml (IU/ml).

EXAMPLE 1

Effect of High Dose Interferon On Survival Following Lethal Challenge With EMCV (Encephalomyocarditis virus)

The effects of IFN-α doses of 1,000, 10,000 and 100,000 IU given by the oromucosal route was tested in male and female mice injected with a lethal dose of EMCV. Different types of IFN-α were tested, and the effect of administration by the oromucosal route was compared with that of administration by the intraperitoneal (ip) route. In addition to monitoring survival following the lethal challenge, the toxicity of the IFN treatment was monitored using a variety of clinical chemistry and haematological parameters.

Treatment of mice with $10^5$ IU of IFN-α by the oromucosal route once a day for 4 days resulted in complete protection of all the animals, when treatment was started after virus infection. One hundred percent of the IFN treated animals were alive and well 100 days after infection with a lethal dose of EMCV (100 $LD_{50}$) under conditions where all the virus-infected untreated control animals were dead by 7 days.

Based on body weight, treatment of mice with $10^5$ IU by the oromucosal route is equivalent to a human dose of 240 million IU, which to our knowledge is considerably more than has ever been administered in man.

As treatment of mice with $10^5$ IU of IFN-α by the in/or route resulted in a greater degree of protection than treatment of animals with $10^4$ IU of INF-α, it is probable that even greater effects (against an even greater virus load or tumour burden) will be obtained with even higher doses of IFN-α. So far we have not observed any indication of a plateau in the dose-response curve.

Our results also demonstrate that high to ultra-high doses of IFN given by the in/or route have a highly protective antiviral effect, and that $10^5$ IU of IFN-α given by this route gives a complete cure versus the dose of EMCV used. Despite the fact that the doses used were far higher on a body weight basis than those which have ever been administered to humans, being equivalent to $240\times10^6$ IU, no clinical, biochemical or haematological evidence of toxicity was observed.

EXAMPLE 2

Effect of High Dose IFN-α on Mice Challenged with Highly Metastatic Tumour Cells Groups of 10, six week-old DBA/2 mice were challenged intravenously either with $10^5$ Friend erythroleukaemia cells of the interferon-resistant clone 3CI8 or with $10^5$L1210 lymphoma cells (interferon-resistant L1210R cells) on day 0. Following inoculation, the mice were either left untreated, or treated twice a day for 20 days by the in/or route with $10^5$ IU of mouse IFN-α/β in a volume of 10 µl of excipient, or with 10 µl of excipient alone (control).

Fifty percent of the animals treated with IFN by the in/or route were alive and well 100 days after inoculation with the highly metastatic Friend erytlroleukaemia cells. Thirty percent of the animals treated with IFN by the in/or route were alive and well 100 days after challenge with L 1210 lymphoma cells. Clinical observations suggest that all of the IFN-treated animals alive at 100 days would have survived for a normal lifespan if not sacrificed. Histological examination of organs showed absence of residual tumors. In contrast, all the untreated and control animals were dead by 13 days after challenge with Friend erythroleukaemia cells and 14 days after challenge with L1210 lymphoma cells, respectively.

These results are highly significant, since both of the tumour cell lines used are highly aggressive, and since the challenge dose used was equivalent to approximately 20,000 times the $LD_{50}$. Furthermore, Friend Leukaemia and L1210 lymphoma are quite different tumour types, in that Friend Leukaemia cells carry a retrovirus, the Friend Leukaemia virus, while L1210 lymphoma is not associated with any known viral etiology. The results obtained with in/or IFN-α therapy of animals inoculated with L1210 lymphoma appear to be equal to or even superior to those obtained with systemic IFN-α therapy in this model (I. Gresser, unpublished results). In the study reported in Australian provisional application No PN9765, none of the mice inoculated with Friend Leukaemia cells and treated with 100 or 1,000 IU of IFN-α survived, and at a dose of 10,000 IU only 10–20% of the animals were considered to be cured.

EXAMPLE 3

Effect of High Dose IFN-α on Mice Challenged with Highly Metastatic B16 Melanoma Cells or EL4 Tumour Cells Groups of 10 six week-old C57B1/6 mice were challenged intravenously with either $10^5$ B16 melanoma cells, or $10^5$ EL4 tumour cells. Following inoculation, the mice were either left untreated, or treated twice a day for 20 days by the in/or route with $10^5$ IU of mouse IFN α/β in a volume of 10 μl of excipient or with 10 μl of excipient alone (control).

Thirty percent of the animals treated with IFN by the in/or routes were alive and well 100 days after inoculation with highly metastatic B16 melanoma cells or EL4 tumour cells. In contrast, all the untreated and control animals were dead by 20 days after challenge with B16 melanoma cells and 22 days after challenge with L4 tumour cells, respectively. Clinical observation suggests that all of the IFN-treated animals alive at 100 days would have survived if not sacrificed, even though interferon treatment was stopped at 20 days. Histological examination of organs showed the absence of residual tumor in interferon treated animals sacrificed at 100 days.

EXAMPLE 4

Effect of Oromucosal Interferon Against Vesicular Stomatitis Virus

Groups of ten, 6 week-old mice, from a specific pathogen-free breeding colony were infected intranasally with 100 LD50 of Vesicular Stomatitis virus (VSV) (Tovey et al, *Proc. Soc. Exp. Biol. Med.*, 1974, 146:406–415), in a volume of 10 μl. Seven hours after virus infection mice were either left untreated, or treated once a day for 4 days by the intranasal/oral route with a given dose of murine interferon α/β in a volume of 10 μl of Ferimmune excipient, or with 10 μl of excipient alone (control).

Treatment of adult mice with murine interferon α/β resulted in a marked increase in the percentage of animals surviving infection with a lethal dose of VSV. Thus, 30% of the animals treated with 10,000 IU of interferon α/β were alive 21 days after infection with a lethal dose of VSV, under conditions where all the untreated, or excipient control treated virus-infected animals were dead at 10 days. Clinical observations suggest that most of the interferon-treated animals alive at 21 days will survive.

EXAMPLE 5

Effect of Oromucosal Interferon on Expression of Cellular Proteins

IFN-α is known to induce the expression of a number of cellular proteins following binding of the protein to its cell surface receptor. These proteins are thought to provide a useful marker of IFN action.

We evaluated the effect of IFN-α administered via the in/or route on the expression of three IFN-induced proteins, MHC class I antigens, Ly 6A/E antigen and 2'-5'-oligoadenylate synthetase.

Treatment of DBA-2 mice (H-2K$^d$) with up to 20,000 IU of Mu IFN-α by the in/or route did not significantly increase H-2-K$^d$ expression on peripheral blood lymphocytes, monocytes or granulocytes under conditions where as little as 20 IU of Mu IFN-α given ip markedly increased the expression of H-2-K$^d$ antigens on both peripheral blood monocytes and granulocytes. Indeed, expression on monocytes was slightly suppressed.

Similarly, treatment of mice with up to 20,000 IU of IFN-α via the in/or route had no significant effect on the expression of Ly6 A/E antigens, the expression of which is markedly enhanced on the surface of a variety of lymphoid cells following parenteral treatment with type I IFN (Dumont et al; *J. Immunol*, 1986 137: 201–210). Similar results were obtained with 200 or 20,000 IU of either Mu IFN-α or Hu IFN-α 1–8 via the in/or route.

Treatment of either Swiss or DBA/2 mice with as little as 20 IU of Mu IFN-α injected ip resulted in a marked increase in 2'-5'-oligoadenylate synthetase activity in both peripheral blood mononuclear cells and splenocytes. In contrast, in the same experiment treatment of mice with up to 20,000 IU of Mu IFN-α via the in/or route did not significantly increase the expression of 2'-5'-oligoadenylate synthetase activity. Furthermore, treatment with 200 or 20,000 IU of either Mu IFN-α or Hu IFN-α 1–8 by the in/or route had no significant effect on 2'-5'-oligoadenylate synthetase activity at any of the time points tested up to 10 days after the start of IFN treatment.

EXAMPLE 6

Bioavailability of Interferon Following Oromucosal Administration

In order to examine the bioavailability and pharmacokinetics of IFN, mice, which have the most favorable drug-blood volume ratio for such studies, were treated with a single high dose of recombinant IFN-α labeled to the highest specific radioactivity possible with $^{125}$I.

A pure preparation of $70 \times 10^6$ IU of Hu IFN-α 1–8 was taken up in 1.4 mls of PBS, and iodinated as described by Mogensen et al, (*Int. J. Cancer*, 1981 28: 575–582) using a modification of the chloramine-T method described by Hunter and Greenwood (*Nature*, 1962 194: 495–496).

The $^{125}$I-labeled Hu IFN-α 1–8 (lot no. CGP35269-1) exhibited a biological activity of $2 \times 10^7$ IU/ml when assayed on human WISH cells challenged with VSV and $1 \times 10^6$ IU/ml when assayed on mouse L929 cells challenged with VSV.

Six to seven week-old female Swiss mice were injected iv, ip, or treated in/or with $2 \times 10^7$ IU equivalent to $1 \times 10^6$ murine IU of $^{125}$I Hu IFN-α 1–8 ($1.0369 \times 10^7$ cpm/mouse). At the time points indicated, three mice per group were sacrificed, blood was collected, and the volume determined. Kidney, liver, lung, spleen, and stomach/esophagus were harvested, blotted, and weighed to a precision of ±1.0 μg. The radioactivity of each sample was determined individually using a gamma counter. Whole blood was then separated by centrifugation (800g×10 min., 4° C.), the serum was harvested, counted, and frozen at −80° C. The serum was then assayed for IFN content using a standard bioassay on both human WISH cells and on mouse L929 cells as described above. The radioactive material present in the samples of serum was then isolated by affinity immunoprecipitation and analyzed by SDS-PAGE.

Very high levels of radioactivity (>$2 \times 10^6$ cpm/ml) were detected in the peripheral blood of animals 5 min. after injection of 1.0369×10⁷ cpm/mouse of ¹²⁵I-labeled Hu IFN-α 1–8 by iv bolus. The amount of radioactivity present in whole blood then declined progressively at 15 and 30 min. The levels of radioactivity detected in the peripheral blood of animals 5 min. after ip injection of 1.0369×10⁷ cpm of $^{125}$I Hu IFN-α-1–8 were approximately twenty fold lower than the levels detected following an iv bolus. The levels of radioactivity then increased progressively at 15 and 30 min. post-injection. The levels of radioactivity detected in the blood of animals at 5, 10 or 15 min. after the in/or administration of $^{125}$I IFN-α 1–8 were significantly lower than those detected at a given time following ip injection of the same quantity of radiolabelled IFN. For all three routes of administration, higher levels of radioactivity were detected in serum than in whole blood following in/or administration of $^{125}$I-labeled IFN-α 1–8. The lower levels of radioactivity detected per ml of whole blood compared with the same volume of serum reflect the effectively larger volume of serum counted after removal of the cellular component of whole blood.

Samples of serum from all the mice in the study were assayed for the presence of biologically active IFN using a standard bioassay, as described above, and showed readily detectable levels of biologically active IFN in the serum of all the animals injected either iv or ip with $^{125}$I Hu IFN-α 1–8 at all the time points tested. In contrast, no biologically active IFN was detected in the serum of any of the animals at any of the time points tested following the in/or administration of IFN, in spite of the presence of relatively high levels of radioactivity in the serum of these animals.

In order to determine whether the radioactive material detected in the serum of animals treated with $^{125}$I Hu IFN-α 1–8 does indeed represent native IFN, the samples were immunoprecipitated with protein A–G Agarose, in order to precipitate immunoglobulins present in the samples, treated with an affinity-purified polyclonal anti-IFN-αantibody, and further immunoprecipitated. The samples were then subjected to SDS-polyacrylamide gel electrophoresis (SDS-PAGE) as described above.

SDS-PAGE analysis of the radioactive material in serum following iv or ip injection of $^{125}$I Hu IFN-α 1–8 revealed a single homogenous band migrating with an electrophoretic mobility identical to that of uninjected $^{125}$I Hu IFN-α 1–8. The apparent molecular weight of the material was estimated to be approximately 20000 Daltons, which corresponds exactly to the molecular weight of native Hu IFN-α 1–8. In contrast, none of the samples of serum from mice treated in/or with $^{125}$I IFN-α 1–8 contained any material with an apparent molecular weight similar to that of native IFN, even though an identical quantity of radioactive material was loaded on to each gel.

The tissue distribution of radiolabelled material revealed very high levels of radioactivity in the kidneys, high levels in the liver, lung, and spleen of animals 5 min. after the iv injection of $^{125}$I IFN-α 1–8. The level of radioactivity present in each of these four organs was then found to decrease progressively at 15 and 30 min. In contrast, the level of radioactivity in the stomach increased progressively at 15 and 30 min. to reach a level comparable to that present in the serum of animals 30 min. after an iv bolus.

Administration of $^{125}$I IFN-α 1–8 by ip injection resulted in peak levels of radioactivity in all the tissues examined within 15 min., followed by a decline at 30 min. Similarly, in/or administration of $^{125}$I Hu IFN-α 1–8 resulted in peak levels of radioactivity in all the tissues studied after 15 min. with some decline in the levels of radioactivity present at 30 min. The levels of radioactivity present in the stomach/esophagus were an order of magnitude greater than those detected in any other organ following the in/or administration of $^{125}$I-labeled IFN-α 1–8, and were markedly higher than the levels present in these tissues following parenteral administration of the same quantity of radiolabelled Hu IFN-α 1–8 by either the iv or ip routes.

EXAMPLE 7

Pharmacokinetics of Interferon Following Intranasal/Oral Administration

For precise determination of the pharmacokinetics of Hu IFN-α 1–8, mice were treated iv, ip or in/or with 1.0369×10⁷ cpm/mouse of $^{125}$I-labeled Hu IFN-α 1–8, and the levels of radioactivity present in both whole blood and serum were determined at a series of time points over a 24 hour period.

The pharmacokinetic profile of $^{125}$I-labeled Hu IFN-α 1–8 present in the blood of mice after an iv bolus closely followed a logarithmic clearance curve. This agreed with results of a previous study carried out in mice using a closely related molecule, recombinant human α A/D (Bgl) (Bohoslawed et al; *J. IFN Res.*, 1986 6: 207–213). The amount of bioavailable material, calculated from the area under the curve of concentration versus time, was also similar to that for human α A/D. A biphasic time-consuming clearance curve was observed following an iv bolus of $^{125}$I IFN-α 1–8, which is characteristic of substances which are cleared through the kidneys, in agreement with the results of Example 6. The pharmacokinetics of $^{125}$I-labeled IFN-α 1–8 following ip injection closely resembled those previously reported for IFNs administered im.

Readily detectable levels of biologically active IFN were present in the serum of all the animals following either an iv bolus or ip injection of $^{125}$I-labeled IFN-α 1–8.

1. Discussion of Anti-tumor Activity

The Friend erythroleukaemia model constitutes a very severe preclinical test of anti-tumor activity, since FLC are highly malignant and metastasize to both the liver and spleen when injected iv. Indeed, results obtained using this model were the basis for the adoption of parenteral injection of IFN-α for treatment of human cancers. Thus, in all the experiments carried out in this study all the untreated animals and animals treated with control preparations died within 10 to 11 days. Injection of only 4 or 5 FLC cells will kill a mouse if no treatment is given. In contrast, some of the animals treated with murine IFN-α by the oromucosal route are still alive more than 100 days after inoculation of 10⁵ FLC, and may be considered to be cured.

Indeed, judging from previous work, IFN-α administered by the oromucosal route appears to be more effective than cyclophosphamide, 5-fluorouracil, or methotrexate administered parenterally, which increase survival time by only a few days in animals injected with FLC (Gresser et al,*J. Natl. Cancer Inst.*, 1988 80: 126–31). Other drugs, such as cisplatin, vincristine, doxorubicin, bleomycin or etoposide are ineffective against this tumor (Gresser et al, *J. Natl. Cancer Inst*, 1988 80: 126–131).

Similarly, IFN-α administered by the oromucosal route appears to be more effective against FLC than other cytokines such as IL-1β, IL-2 and TNF-α administered systemically, which exhibit very little activity in this model.

Previous work has shown that IFN administered parenterally is one of the most active anti-tumor drugs in this model, and that IFN therapy is effective even when initiated after tumor metastases are already present in the liver (Gresser et al, *Intl. J. Cancer*, 1987 39: 789–792). The present results show that IFN administration by the oromucosal route is equally, or even more, effective.

Daily injections of IFN-α given together with a single dose of cyclophosphamide markedly increased the survival of lymphoma-bearing AKR mice compared to animals treated with either agent alone, when therapy was started after diagnosis of the lymphoma (Gresser et al, *Eur. J. Cancer*, 1978 14: 97–99). Successful combination therapy using IFN-αZβ and BCNU, cis-DDP (cisplatin), methotrexate, adriamycin, and α-difluoromethyl ornithine has also been reported in various pre-clinical animal tumor models. Combination therapy with 5-fluorouracil (5-FU) and IFN has also been reported to be of benefit in the treatment of metastatic colon cancer in man (Ernstoff et al, *Journal of Clinical Oncology*, 1989 7: 1764–1765). There are, however, other studies which have reported a decreased anti-tumor activity when IFN therapy was combined with the use of cyclophosphamide (Marquet et al, *Int. J. Cancer*, 1983 31: 223–226; Lee et al, *Biochem. Pharmacol.*, 1984 33: 4339–3443), adriamycin (Blackwill et al, *Cancer Res.*, 1984 44: 904–908), or 5-FU (Marquet et al, 1985 109: 156–158), i.e. precisely the same drugs which have been shown to exert a beneficial effect when used in combination with parenteral IFN therapy. Combinations between IFN and other chemotherapy agents can readily be tested using methods described herein.

Combined interleukin-1 (IL-1) and IFN-α/β therapy results in a synergistic anti-tumor effect in mice injected with FLC (Belardelli et al, *Int. J. Cancer*, 1991 49: 274–278). The same treatment also exerts a marked anti-tumor effect against a metastatic variant (p11-R-Eb) of the Eb lymphoma, against which either agent alone is ineffective (Gabriele et al, *Invasion Metastasis*, 1993 13: 147–162). Of all the cytokines tested, IL-1 was found to be the most effective when combined with parenteral type I IFN therapy.

Combination therapy with the angiogenesis inhibitor AGM-1470 [(Chloroacetyl)-carbamic acid (3R-(3α, 4α (2R*, 3R*), 5β, 6β))-5-methoxy-4-(2-methyl-3-(3-methoxy-2-butenyl)oxiranyl)-1-oxaspiro(2.5)oct-6-yl ester] given together with IFN-α/β resulted in a markedly increased anti-tumor effect compared to that observed with either agent alone (Brem et al, *J. Pediatric Surgery*, 1993 28: 1253–1257).

It has been shown that hyperthermia enhances the anti-tumor action of IFN-(α/β) against the Lewis lung carcinoma (Yerushalmi et al, *Proc. Soc. Exp. Biol. Med.*, 1982 169: 413–415). Arginine butyrate has also been shown to potentiate the anti-tumor action of IFN-α (Chany and Cerutti, *Int. J. Cancer*, 1982 30: 489–493).

Comparison of the degree of protection obtained when a given type and dose of IFN was administered by the oromucosal route compared to the results obtained following systemic administration (ip injection) showed that parenteral administration of IFN was in some cases marginally more effective, and in other cases no more effective, than oromucosal administration.

2. Discussion of Antiviral Activity

Although antiviral activity could not be detected in the serum of animals following in/or administration of $^{125}$I IFN-α 1–8, Mu IFN-α/β and Mu IFN-α a statistically significant degree of protection against infection with a lethal dose of EMCV was nevertheless observed in these animals. Our results obtained in a well-defined preclinical model of acute viral infection provide unequivocal evidence to support the "proof of principle" for the use of high dose oromucosal IFN for the therapy of acute systemic viral infections in man, and show that both a natural mixture of multiple IFN-α subtypes and a single recombinant IFN-α isotype (for example Mu IFN-α) exert statistically significant antiviral activity in this model. Natural Mu IFN-α/β and Hu IFN-α 1–8 appeared to be equally effective when administered oromucosally. Recombinant Mu IFN-β and Mu IFN-γ also show similar antiviral activity.

Comparison of the degree of protection obtained when a given type and dose of IFN was administered by the oromucosal route compared to the results obtained following systemic administration (ip injection) showed that parenteral administration of IFN was in some cases marginally more effective, and in other cases no more effective, than oromucosal administration.

3. General Discussion

The results of the biomarker pilot study show quite clearly that none of the three biomarkers tested (MHC class I antigen, Ly6 A/E antigen, and 2'-5'-oligoadenylate synthetase activity) adequately reflects the very marked biological activity (for example, antitumoral and antiviral activity) exhibited by IFN-α administered by the oromucosal route.

The contrast between the very marked increase in the expression of all three IFN-induced proteins observed in all the experiments undertaken following the ip injection of as little as 20 IU of IFN-α and the absence of any detectable effect following the administration of up to 20,000 IU of IFN-α via the oromucosal route is striking.

Although we cannot exclude the possibility that an effect on one or other of the biomarkers would have been observed at an earlier or intermediate time point, this seems to be unlikely, as IFN acts on the transcription of the genes coding for these proteins and thus one would not expect to see an effect on any of these biomarkers until a number of hours after IFN treatment.

Again, although we cannot exclude the possibility that a systemic effect on one of the other numerous IFN-induced proteins would have been observed following treatment with IFN-α by the oromucosal route, this seems unlikely, as this would imply differential regulation of the expression of certain IFN-induced genes. It is entirely possible, however, that an effect on an IFN biomarker may be observed locally, for example, in nasal lymphocytes following administration of IFN-α via the oromucosal route.

In keeping with the absence of a detectable effect on the biomarkers studied, no consistent effect was observed on any of the hematological or blood chemistry parameters monitored during oromucosal IFN therapy, even in animals treated with up to 100,000 IU of IFN-α.

The results of the pharmacokinetics-bioactivity study show quite clearly that a statistically significant antiviral effect can be obtained following the oromucosal administration of a single dose of radiolabelled Hu IFN-α 1–8 under conditions where no circulating IFN can be detected in the peripheral blood, using methods of detection which are an order of magnitude more sensitive than those used previously. In keeping with these results the extent of the antiviral activity exerted by oromucosally administered IFN appeared to follow a classical dose-response relationship.

Readily detectable levels of radiolabelled material were found in both whole blood and serum of animals following oromucosal administration of $^{125}$I-labeled IFN-α 1–8. These results contrast with the results of previous studies, which failed to detect IFN in the serum of animals even after the oral administration of large quantities of unlabelled IFN.

However, the radioactive material detected in both whole blood and serum following oromucosal administration was biologically inactive. Furthermore, the results of SDS-PAGE analysis showed that this material was of low molecular weight, and most probably reflected the absorption of degradation products following digestion of IFN in the stomach and small intestine. Analysis of the tissue distribution of radiolabelled material following oromucosal administration revealed markedly higher levels of radioactivity in the stomach than in any of the other organs tested. Our results show quite clearly that even though biologically active IFN was not absorbed following oromucosal administration, this treatment does nevertheless exert a statistically significant antitumor and antiviral activity in vivo.

Without wishing to be bound by any proposed mechanism for the observed beneficial effect, our results suggest that oromucosally administered IFN exerts its effects against tumor cells or against viruses via a presently undefined novel mechanism, which does not involve a direct action of exogenously administered IFN, or the induction of endogenous IFN. This is supported by the absence of detectable levels of circulatory IFN or of the three biomarkers tested. It appears that this mechanism may act at least partly by stimulation of the abundant lymphoid tissue surrounding the nasopharyngeal and oral cavities. Since we have shown that oromucosal IFN is at least comparable in efficacy to systemically administered IFN, our results provide strong support for administration of IFN by the oromucosal route in the treatment of neoplastic or viral disease. This could have important implications for the clinical use of IFN.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

What is claimed is:

1. A method for treating a neoplastic condition sensitive to interferon, which method comprises administering to the mammal an effective amount of an interferon via oromucosal contact, said amount being in excess of a dose of the same interferon which induces a pathological response when parenterally administered.

2. A method of claim 1 wherein the neoplastic condition is of non-viral etiology.

3. The method of claim 1, in which the effective dose of interferon is administered in a single dose.

4. The method of claim 1, in which the effective dose of interferon is administered in a plurality of smaller doses over a period of time sufficient to elicit a response equivalent to that of a single dose.

5. The method of claim 1, in which an effective dose of interferon is administered continuously over a period of time sufficient to elicit a response equivalent to that of a single dose.

6. The method of claim 1, wherein the interferon comprises a Type I interferon.

7. The method of claim 6, wherein the interferon is selected from the group consisting of IFN-α, IFN-β, IFN-ω, consensus IFN, and mixtures thereof.

8. The method of claim 7, wherein the IFN-α comprises recombinant IFN-α.

9. The method of claim 1, wherein the interferon comprises a Type II interferon.

10. The method of claim 9, wherein the Type II interferon comprises IFN-γ.

11. The method of claim 1, wherein the dose of interferon is greater than $20 \times 10^6$ IU to about $1000 \times 10^6$ IU of interferon.

12. The method of claim 1, wherein the dose of interferon is greater than $20 \times 10^6$ IU to about $500 \times 10^6$ IU of interferon.

13. The method of claim 1, wherein the dose of interferon is from about $50 \times 10^6$ IU to about $500 \times 10^6$ IU of interferon.

14. The method of claim 1, wherein the neoplastic condition is selected from the group consisting of renal cell carcinoma, bladder cancer, cervical cancer, malignant melanoma, multiple mycloma, Kaposi's sarcoma, hairy cell leukemia, non-Hodgkin's lymphoma, chronic myeloid leukemia, nasopharyngeal carcinoma, breast cancer, large bowel (colon) cancer, uterine cancer, head and neck cancers, glioblastoma, cutaneous T-cell lymphoma, basal cell carcinoma, brain Tumors, and lung cancer.

15. A method in accordance with claim 1, wherein said administering step comprises bringing said interferon into contact with the mucosa lining the mouth and/or throat of the mammal being treated.

* * * * *